US006913585B2

United States Patent
Salmon et al.

(10) Patent No.: US 6,913,585 B2
(45) Date of Patent: Jul. 5, 2005

(54) ADJUSTABLE COMPACT POSTURE PACK FOR POSTERIOR-THORACIC COUNTER BALANCE

(75) Inventors: Kirt Salmon, St. George, UT (US); Kris Hansen, St. George, UT (US)

(73) Assignee: C. Kirt Salmon, St. George, UT (US)

(*) Notice: Subject to any disclaimer, the term of this patent is extended or adjusted under 35 U.S.C. 154(b) by 266 days.

(21) Appl. No.: 10/349,261

(22) Filed: Jan. 21, 2003

(65) Prior Publication Data

US 2004/0143204 A1 Jul. 22, 2004

(51) Int. Cl.[7] .................................................. A61F 5/00
(52) U.S. Cl. ........................ 602/19; 128/874; 128/875
(58) Field of Search ................ 602/5, 19; 128/874–876

(56) References Cited

U.S. PATENT DOCUMENTS

| | | | |
|---|---|---|---|
| 3,013,561 A | 12/1961 | Nelkin | 450/128 |
| 4,099,524 A | 7/1978 | Cueman et al. | 128/78 |
| 4,332,379 A | 6/1982 | Bannister | 272/119 |
| 4,394,012 A | 7/1983 | Egbert et al. | 272/119 |
| 4,674,664 A | 6/1987 | Simon | 224/215 |
| 4,948,122 A | 8/1990 | Andrews | 272/119 |
| 5,067,484 A | 11/1991 | Hiemstra-Paez | 128/78 |
| 5,120,288 A | 6/1992 | Sinaki | 482/105 |
| 5,205,672 A * | 4/1993 | Stinton | 405/186 |
| 5,240,157 A * | 8/1993 | Selhost | 224/639 |
| 5,713,840 A | 2/1998 | Brentham | 602/19 |

* cited by examiner

Primary Examiner—Michael A. Brown

(57) ABSTRACT

A novel adjustment compact posture pack for posterior-thoracic counter balance (13) comprising of a stationary weight pack (32) having a right shoulder strap (14) having an adjustment device (18), a left shoulder strap (15) having an adjustment device (19) a lower center-rear strap (16) having a single strap connector (24), an upper center-rear strap (17) having an adjustment device (26). Each strap having one end attached to top edge of stationary weight pack (32) at coordinated locations with other end connected to a common 3-way strap connector (20). Stationary weight pack (32) having at least one upper stationary pocket (34) containing at least one weight material (37) and at least one lower stationary pocket (35) containing at least one weight material (38) a first member attachment device (40) attached to backside of stationary weight pack (32) and a removable weight pack (33) having at least one removable pocket (36) containing at least one weight material (39) and a second member attachment device (41) attached to the horizontal center of front side of removable weight pack (33). When the first and second member attachment device (40) and (41) are hand pressed together they attach to each other and when a pulling hand pressure is applied by the user to the removable weight pack (33) the first and second member attachment devices (40) and (41) detach. The removable weight pack (33) can be reattached to the stationary weight pack (32) as desired by the user.

6 Claims, 5 Drawing Sheets

ADJUSTABLE COMPACT POSTURE PACK FOR POSTERIOR-THORACIC COUNTER BALANCE

BACKGROUND

1. Field of Invention

This invention relates in general to a weighted device providing a counter balance to the posterior-thoracic spine causing proper posture in the shoulder area by pulling the shoulder posterior back and inward toward the spine.

2. Description of Prior Art

Prior art have not taken into account for pulling the shoulder area back and inward toward the spine. My invention has a back adjustable strap which holds in place the shoulder straps in the proper position and allows the user to adjust as required the location of the weight pack located on the back area of the user.

My invention has an advantage over all prior art because of the location of the 3-way strap connector on the back center strap which allows the shoulder straps to be attached at an angle on said 3-way strap connector giving the shoulder straps the proper position by adjusting the said 3-way strap connector on the center back strap which is a novel feature which the prior art does not have.

Another type weighted lumbar support is designed to apply pressure to the lumbar region of a user when the user is seated in a chair the lumbar support applies pressure to prevent realignment of the user's lower spine for maintaining proper posture. My invention is used to pull the users shoulder area back and inward toward the spine. This is done while the user is standing, walking or setting in a chair or in every day activity. This makes my invention more practicable because of the novel feature of being able to use my invention in every day activity.

Another type posture training support comprises a pouch for holding one or more weights. The pouch is positioned on the back of the user below the inferior angle of the user's scapulae by means of adjustable clavicle straps secured to the pouch. This invention does not leave a center back adjustable strap with a 3-way connector thereby not having the ability to adjust the shoulder straps in a position that would hold the shoulder straps in the proper position. This invention the shoulder straps move to the outward direction of the shoulder area and can slip off the shoulder while being used by the user. Whereby my invention can't slip off the shoulder because of the unique 3-way strap connector which holds the shoulder straps from moving to the outward direction of the shoulder.

Another type posture training support with weight pockets is designed the same as the prior mentioned invention. This invention also does not have a center back adjustable strap with a 3-way strap connector, thereby not having the ability to adjust the shoulder straps in a position that would hold the shoulder straps in the proper position. This invention has no ability to keep the shoulder straps from moving to the outward direction of the shoulder thereby allowing the shoulder strap to slip off the shoulder. My invention can't do this because of the unique 3-way strap connector on the center back adjustable strap, which holds the shoulder strap from moving to the outward direction of the shoulder. Also my invention has a more positive action on the shoulder area by pulling the shoulder area back and inward toward the spine.

Another type athletic weight harness includes a belt, a torso-protecting shield connected to the belt at the lower end of the torso-protecting shield with a weight attached. This athletic weight harness is used for bodybuilding. It is not used as an adjustable compact posture pack for posterior-thoracic counter balance. This invention has no application to my invention.

Another type backsack including a flexible pouch with an open upper end, and an opposed pair of shoulder straps. This invention has no application to my invention. It was designed as a backsack only, whereas my invention is used to improve shoulder posture. The more the user uses my invention, the better posterior-thoracic posture improves.

Another type weighted exercise vest that selectively allows weight-capsules to be inserted into pockets. The weight capsules are of a uniform size and shape and fit snugly into the weight pockets. Each weight capsule has at least one weight securely held therein. This vest allows free movement of the arms and is adopted to be worn while participating in conventional athletic activities, such as volleyball, basketball, racquetball, tennis and the like. This invention is not designed to be an adjustable compact posture pack for posterior-thoracic counter balance. My invention is used by the user to be an adjustable compact posture pack for posterior-thoracic counter balance to improve shoulder posture.

Another type collapsible exercise backpack to be worn by a person during physical exercise. It includes a flexible weight-carrying member, with at least one opening in the member positioned at its bottom for containing a flexible weight member. Straps attached to the weight-carrying member secures the device about the person's shoulders and waist. This invention is not designed to be an adjustable compact posture pack for posterior-thoracic counter balance, whereas my invention is designed to be an adjustable compact posture pack for posterior-thoracic counter balance.

Another type sacro-lumbar support belt includes an outer face completely covered by a looped fabric and two elastic tightening panels, each panel rigidly coupled at one end to the outer face and having at its other end a hook means for releasable securing that end to the outer surface at any desired location. Pelvic traction straps with hook means at one end are releasable engageable on the belt outer face at any desired location. This invention is not designed to be an adjustable compact posture pack for posterior-thoracic counter balance.

Another type surgical support which relates to a surgical support and more particularly to a belt adapted to be worn by the user for support to the back and abdomen. This invention cannot be used as an adjustable compact posture pack for posterior-thoracic counter balance.

OBJECTS AND ADVANTAGES

Accordingly, besides the objects and advantages described above, several objects and advantages of the present invention are:

(a) to provide a reduction in the overall cost of labor.
(b) to provide a reduction in the cost of materials used.
(c) to provide for a compact unit making it more comfortable when worn for long periods of time.
(d) to provide for a simplistic design with great strength.
(e) to provide a less elaborate design.
(f) it allows the shoulder straps to stay on the shoulder area without sliding off the shoulders.
(g) to provide the user with a more positive way of correcting poor posture.
(h) it allows the user to wear the adjustable compact posture pack for a short period or a long period of time as required by each user.

(i) it allows the user to wear it under or over the users clothing.

(j) it allows the user to adjust the compact posture pack himself or herself as required.

(k) it provides for additional weights if desired that are able to be attached to weight pack as required by each user.

It is an object of the present invention to provide an easier way for an individual who has poor posture to improve his or her posture.

Other objects and features are readily apparent from the following description of certain preferred embodiments thereof taken in conjunction with the accompanying drawings although variations and modifications may be affected without departing from the sphere and the scope of the normal concepts of the disclosed invention. You will find further objects and advantages of this invention from a consideration of the ensuing descriptions and accompanying drawings.

DRAWING FIGURES

Figure 1:
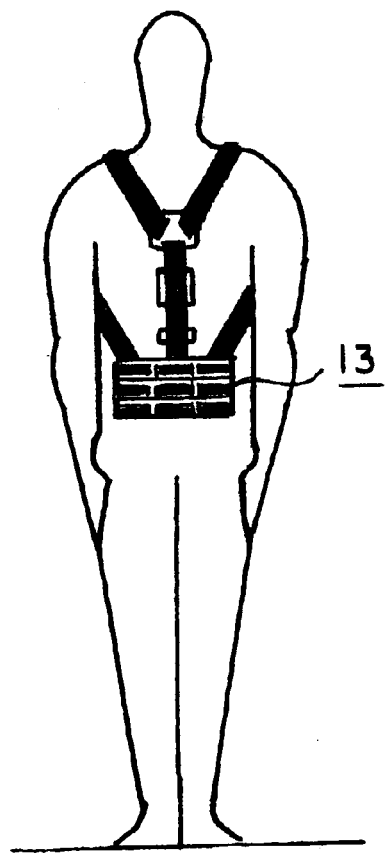
FIG. 1 Shows a rear view of an user wearing the adjustable compact posture pack.

DRAWING REFERENCE NUMERALS 13 adjustable compact posture pack for posterior-thoracic counter balance
14 right shoulder strap
15 left shoulder strap
16 lower center-rear strap
17 upper center-rear strap
18 adjustment device
19 adjustment device
20 3-way strap connector
21 right receiver hole
22 left receiver hole
23 lower receiver hole
24 single strap connector
25 receiver hole
26 adjustment device
27 upper receiver hole
28 lower receiver hole
29 attachment means
30 attachment means
31 attachment means
32 stationary weight pack
33 removable weight pack
34 upper stationary pocket
35 lower stationery pocket
36 removable pocket
37 weight material
38 weight material
39 weight material
40 first member attachment device
41 second member attachment device
42 attachment means
43 attachment means
44 attachment means
45 attachment means
46 attachment means
47 attachment means
48 attachment means
49 attachment means
50 upper receiver hole
51 lower receiver hole
52 upper receiver hole
53 lower receiver hole

DESCRIPTION OF INVENTION

Figure 2:
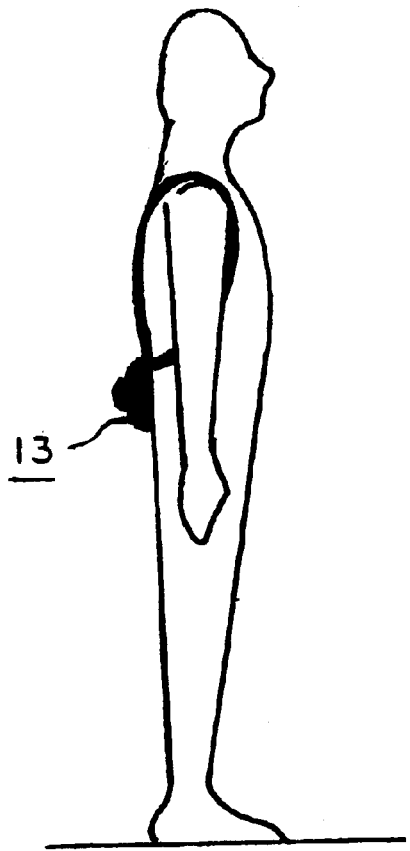
FIG. 2 Shows a side view of an user wearing the adjustable compact posture pack.
Figure 3:
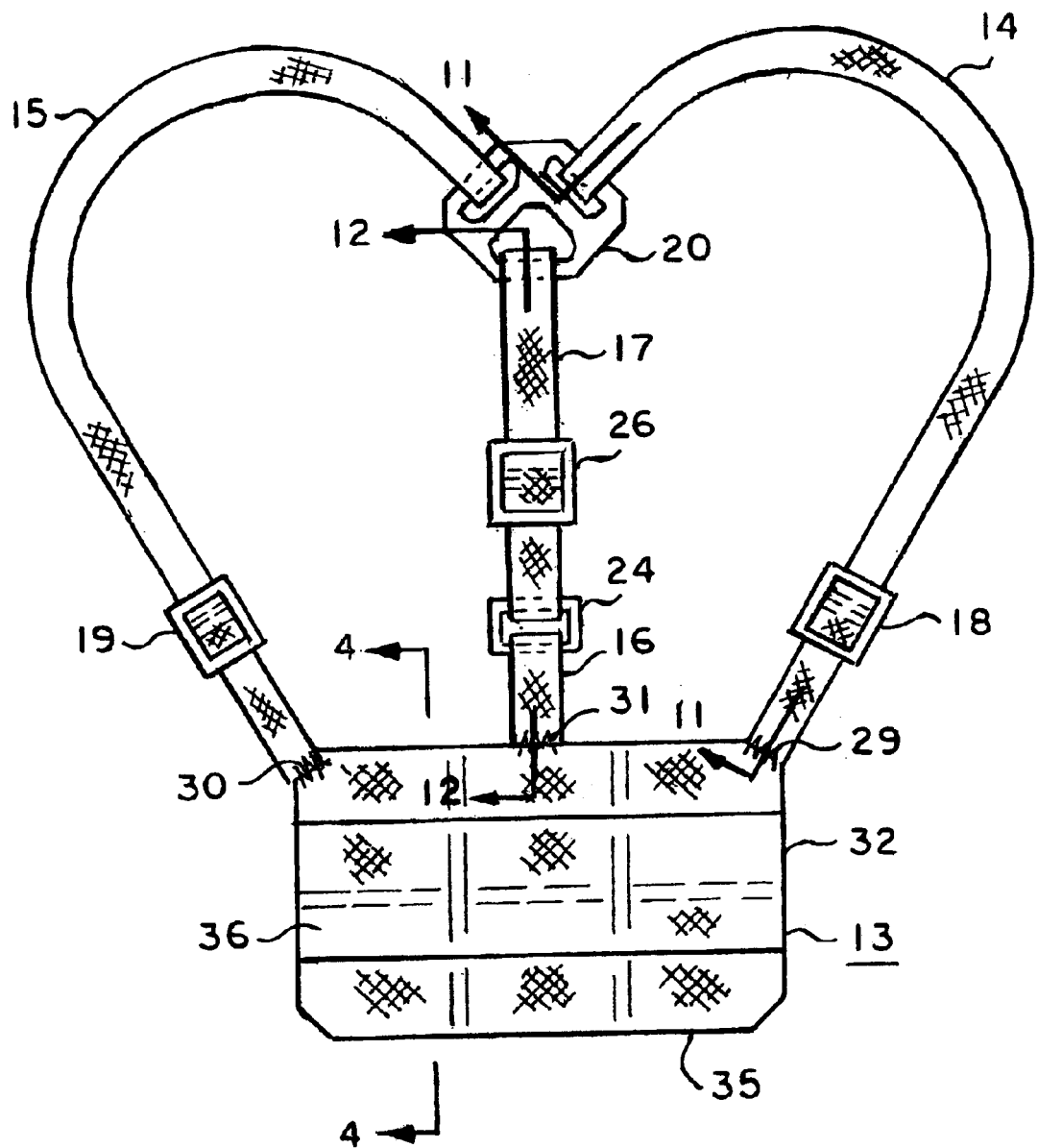
FIG. 3 Shows a rear view of the adjustable compact posture pack.
Figure 4:
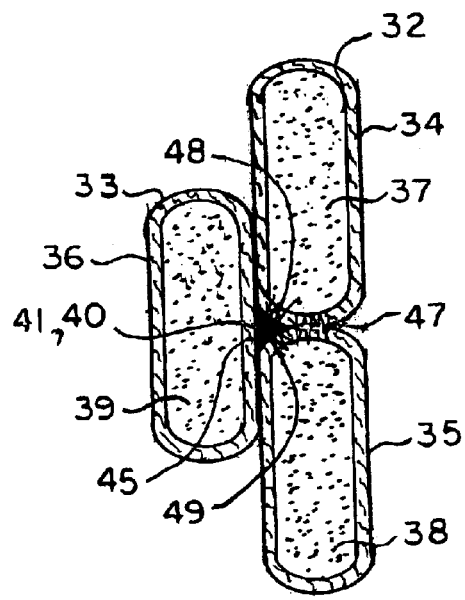
FIG. 4 Shows a cross-section of the stationary and removal weight material pockets areas taken along line 4—4 FIG. 3.
Figure 5:
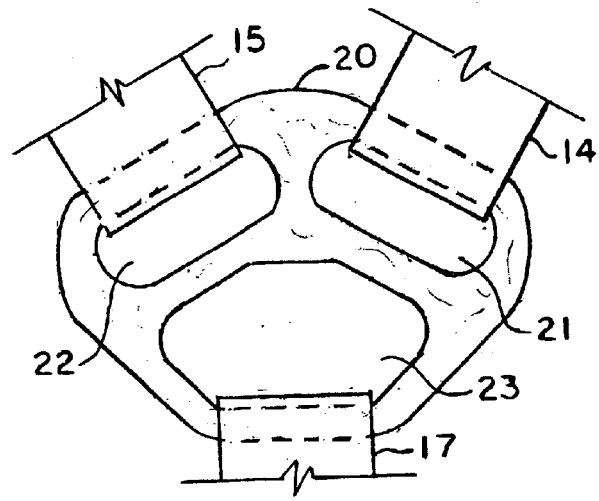
FIG. 5 Shows a front view of the 3-way strap connector.
Figure 6:
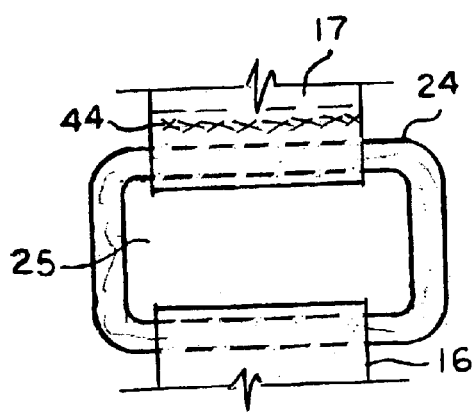
FIG. 6 Shows a front view of the single strap connector.
Figure 7:
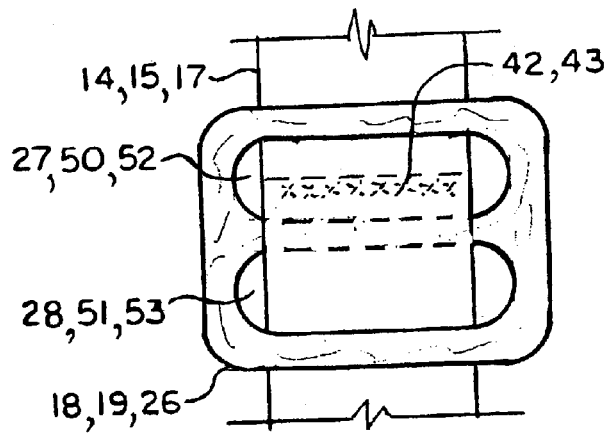
FIG. 7 Shows a front view of the strap adjustable device.
Figure 8:
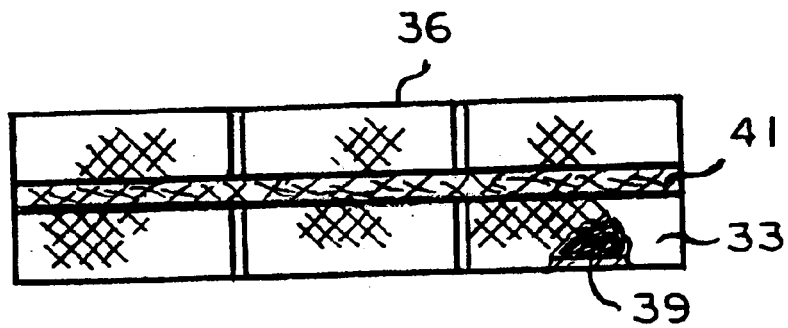
FIG. 8 Shows a front view of the removable weight pack with the second member attachment means.
Figure 9:
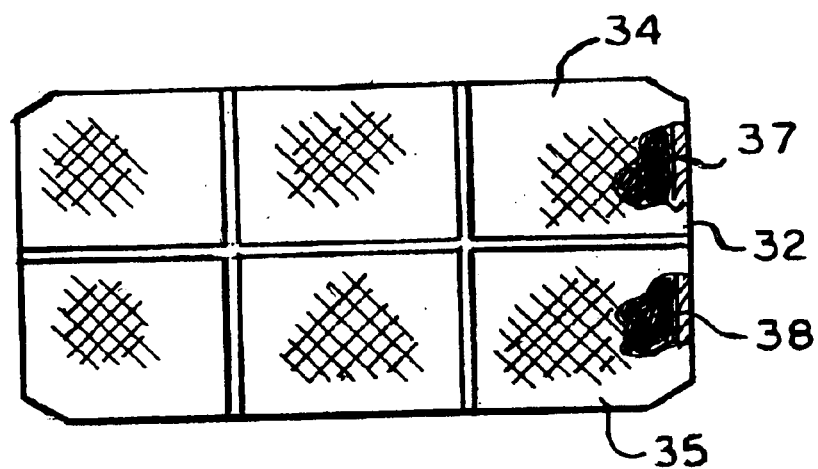
FIG. 9 Shows a front view of the stationary weight pack.
Figure 10:
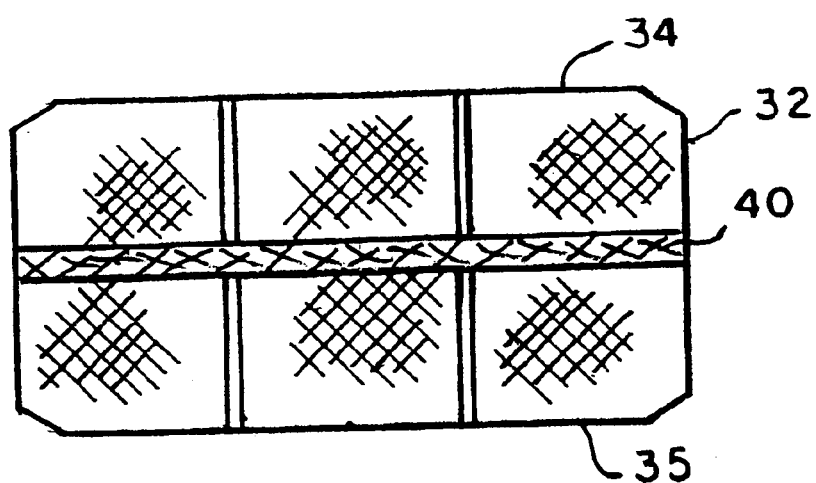
FIG. 10 Shows a rear view of the stationary weight pack with the first member attachment means.
Figure 11:
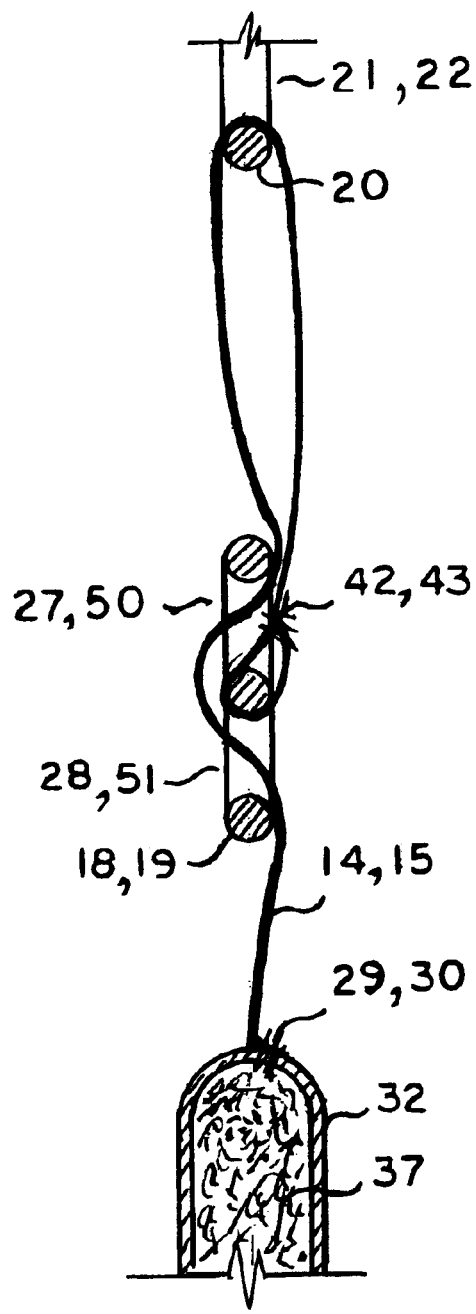
FIG. 11 Shows a cross section of the shoulder straps taken along line 11—11 FIG. 3.
Figure 12:
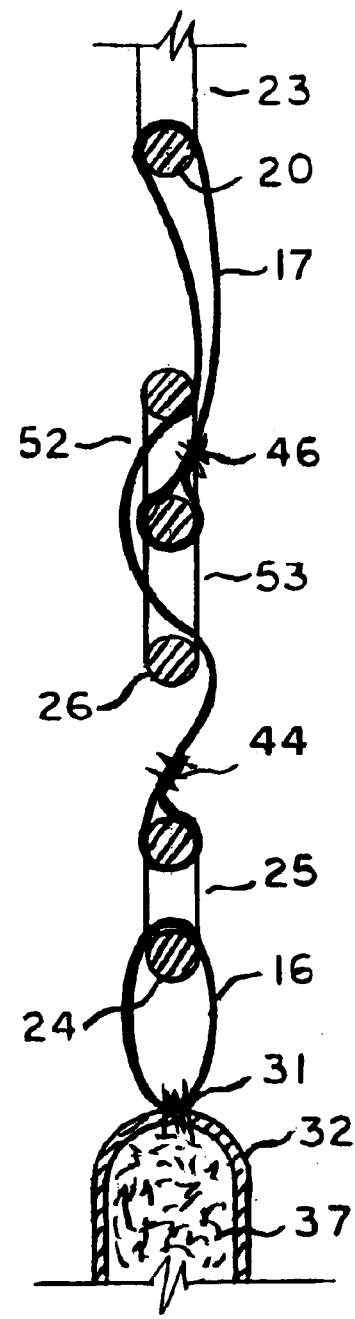
FIG. 12 Shows a cross section of the center back straps taken along line 12—12 FIG. 3.

The adjustable compact posture pack for posterior-thoracic counter balance 13 shown in FIG. 1, FIG. 2, and FIG. 3, comprises of a right shoulder strap 14, shown in FIG. 3, FIG. 5, FIG. 7, and FIG. 11, having sufficient thickness, width and length, with one end attached by attachment means 29 to the upper right hand corner of a stationary weight pack 32 shown in FIG. 3, FIG. 4, FIG. 9, FIG. 10 FIG. 11 and FIG. 12, said right shoulder strap 14 is then routed to an adjustment device 18 shown in FIG. 3, FIG. 5, FIG. 7 and FIG. 11 having sufficient thickness, width and length and having a lower receiver hole 28 and an upper receiver hole 27 shown in FIG. 7 and FIG. 11, said right shoulder strap 14 is received by said lower receiver hole 28, then received by said upper receiver hole 27, said right shoulder strap 14 is routed to a 3-way connector 20 shown in FIG. 3, FIG. 5, FIG. 11 and FIG. 12 having sufficient thickness, width and length, said 3-way connector 20 having a right receiver hole 21 shown in FIG. 5 and FIG. 11 said right shoulder strap 14 is received by said right receiver hole 21 then said right shoulder strap 14 making a 90 degree turn is routed back to said adjustable device 18, said right shoulder strap 14 is received by said upper receiver hole 27 of said adjustable device 18 making a 90 degree turn having sufficient length is attached to itself by attachment means 42 shown in FIG. 7 and FIG. 11, a left shoulder strap 15, shown in FIG. 3, FIG. 5, FIG. 7 and FIG. 11, having sufficient thickness, width, and length with one end attached by attachment means 30 to the upper left hand corner of said stationary weight pack 32 shown in FIG. 3, FIG. 4, FIG. 9, FIG. 10, FIG. 11 and FIG. 12, said left shoulder strap 15 is then routed to an adjustment device 19 shown in FIG. 3, FIG. 7 and FIG. 11 having sufficient thickness, width and length and having a lower receiver hole 51 and an upper receiver hold 50 shown in FIG. 7 and FIG. 11, said left shoulder strap 15 is received by said lower receiver hole 51, then received by said upper receiver hole 50, said left shoulder strap 15 is routed to said 3-way connector 20 shown in FIG. 3, FIG. 5, FIG. 7 and FIG. 11, said 3-way connector 20 having a left receiver hole 22 shown in FIG. 5 and FIG. 11, said left shoulder strap 15 making a 90 degree turn is routed back to said adjustable device 19, said left shoulder strap 15 is received by said upper receiver hole 50 of said adjustable device 19 making a 90 degree turn having sufficient length is attached to itself by attachment means 43 shown in FIG. 11, a lower center-rear strap 16 shown in FIG. 3 and FIG. 12, having sufficient thickness, width and length, having one end attached by attachment means 31 to the upper edge at center of said stationary weight pack 32, shown in FIG. 3, FIG. 4, FIG. 9, FIG. 10, FIG. 11 and FIG. 12, said lower center-rear strap 16 is routed to a single strap connector 24 shown in FIG. 3, FIG. 6 and FIG. 12, having sufficient thickness, width and length having a receiver hole 25, said lower center-rear strap 16 is received at the lower area of said receiver hole 25 of said single strap connector 24, making a 90 degree turn said lower center-rear strap 16 is routed back to the upper edge at center of said stationary weight pack 32 to be attached by said attachment means 31, shown in FIG. 3 and FIG. 12, thereby having both ends of said lower center-rear strap 16 attached to said stationary weight pack 32 at the same time, an upper center-rear strap 17, shown in FIG. 3, FIG. 6, FIG. 7 and FIG. 12, having sufficient thickness, width and length, having one end received at the upper area of said receiver hole 25 of said single strap connector 24 making a 90 degree turn and having sufficient length is attached to itself by attachment means 44 as shown in FIG. 6 and FIG. 12, other end of said upper center-rear strap 17 is routed to adjustment device 26 shown in FIG. 3, FIG. 7 and FIG. 12 having sufficient thickness, width and length, said adjustment device 26 having a lower receiver hole 53 and an upper receiver hole 52, said upper center-rear strap 17 is received by said lower receiver hole 53 then said upper center-rear strap 17 is received by said upper receiver hole 52 as shown in FIG. 12, said upper center-rear strap 17 routed to said 3-way connector 20 is received by lower receiver hole 23 shown in FIG. 5 and FIG. 12, said upper center-rear strap 17 making a 90 degree turn is routed back to said adjustment device 26 said upper center-rear strap 17 is received by said upper receiver hole 52 making a 90 degree turn having sufficient length is attached to itself by attachment means 46 shown in FIG. 12, a stationary weight pack 32 shown in FIG. 3, FIG. 4, FIG. 9, FIG. 10, FIG. 11, and FIG. 12 having sufficient thickness, width and length, having at least one upper stationary pocket 34 being attached to at least one lower stationary pocket 35 having sufficient thickness, width and length by attachment means 47, shown in FIG. 4 said upper stationary pocket 34 containing at least one weight material 37 having sufficient thickness width and length, said lower stationary pocket 35 having at least one weight material 38 having sufficient thickness, width and length, said upper stationary pocket 34 and said lower stationary pocket 35 having a first member attachment device 40 located where said upper stationary pocket 34 and said lower stationary pocket 35 fit together as shown in FIG. 4, said first member attachment device 40 is attached to said upper stationary pocket 34 by attachment means 48 and said first member attachment device is attached to said lower stationary pocket 35 by attachment means 49, as shown in FIG. 4, a removable weight pack 33 having sufficient thickness, width and length having at least one removable packet 36 having sufficient thickness, width and length, containing at least one weight material 39 having sufficient thickness, width and length, said removable weight pack 33 having a second member attachment device 41 located in the horizontal center of said removable weight pack 33 being attached by attachment means 45 as shown in FIG. 4, when said first member attachment device 40 which is attached to said stationary weight pack 32 and second member attachment device 41 which is attached to said removable weight pack 33 are pressed together each attaches itself to the other when removing the said removable weight pack 33 from said stationary weight pack 32 the user applies a pulling pressure on the said removable weight pack 33 causing said first member attachment device 40 and said second member attachment device 41 to detach themselves from each other allowing the said removable weight pack 33 to be removed from said stationary weight pack 32, said removable weight pack 33 may be attached to said stationary weight pack 32 at any future time as desired by the user.

CONCLUSION AND SCOPE OF INVENTION

Accordingly, the reader will see that the adjustable compact posture pack for posterior-thoracic counter balance of this invention functions in a unique manner to produce a utilitarian result. My invention has the ability to cause proper posture in the shoulder area by pulling the shoulder posterior back and inward toward the spine. Furthermore, the adjustable compact posture pack has the additional advantages in that:

- this is a device with weights which provides a counter balance to the posterior-thoracic spine by shoulder straps that come to a center point over the trapeqius and lattisimus dorsii muscles, pulling the shoulders posterior and inward toward the spine, then suspending the counter balancing weight straight down to hang at the lower thoracic spine
- it allows an individual with postural dysfunction to correct this dysfunction by wearing my invention as often as needed.
- it alleviates (because of poor posture) pain syndromes due to increased kyphosis of the thoracic spine and an anterior weight-bearing of the body.
- it allows the user to gain good posture which alleviates pain in the back and neck as well as headache, arm and hand numbness and tingling which can be caused by poor posture.
- it permits the user to stand up straight which can help correct lumbar disc syndromes and nerve impingement which have been shown to result from repetitive end-range flexion overload.
- it allows the user to wear it under or over clothing.
- it provides compactness allowing the adjustable posture pack not to be clumsy when worn by the user.
- it permits quick removal.
- it provides adjustable weight packs
- it provides adjustable shoulder straps allowing the user to adjust to his or her proper requirements.
- it allows the user to add more weight packs if needed.

Although the description above contains many specifications, these should not be construed as limiting the scope of the invention but merely provide illustrations of some of the presently preferred embodiments of this invention. For example, the adjustable compact posture pack shoulder straps, 3-way strap connector, single strap connector, adjustment device, stationary weight pack, or removable weight pack can have other shapes such as square, oval, trapezoidal, triangular, etc. The devices in this invention can be of different combinations of cloth, plastic, leather and metal.

Thus, the scope of the invention should be determined by the appended claims and their legal equivalents, rather than by the examples given.

We claim:

1. An adjustable compact posture pack for posterior-thoracic counter balance which comprises: a stationary weight pack having a right shoulder strap having sufficient thickness, width and length with one end attached by an attachment means to the upper right hand corner of said stationary weight pack, other end of said right shoulder strap is routed to an adjustment device having sufficient thickness, width and length, having a lower receiver hole and an upper receiver hole, said right shoulder strap is received by both holes in such a manner to allow said right shoulder strap to be adjusted to variable lengths, said right shoulder strap is routed to a 3-way connector having sufficient thickness, width and length, having a right receiver hole, said right shoulder strap is received by said right receiver hole then making a 90 degree turn is routed back to said adjustable device then said right shoulder strap is received by said upper receiver hole of said adjustable device making a 90 degree turn having sufficient length is attached to itself by an attachment means.

2. An adjustable compact posture pack for posterior-thoracic counter balance according to claim 1 wherein said stationary weight pack has a left shoulder strap having sufficient thickness, width and length with one end attached by an attachment means to the upper left hand corner of said stationary weight pack, other end of said left shoulder strap is routed to an adjustment device having sufficient thickness, width and length, having a lower receiver hole and an upper receiver hole, said left shoulder strap is received by both holes in such a manner to allow said left shoulder strap to be adjusted to variable lengths, said left shoulder strap is routed to said 3-way connector having a left receiver hole, said left shoulder strap is received by said left receiver hole then making a 90 degree turn is routed back to said adjustable device then said left shoulder strap is received by said upper receiver hole of said adjustable device then said left shoulder strap making a 90 degree turn having sufficient length is attached to itself by an attachment means.

3. An adjustable compact posture pack for posterior-thoracic counter balance according to claim 1 wherein said stationary weight pack has a lower center-rear strap having sufficient thickness, width, and length, having one end attached by an attachment means to the upper edge at center of said stationary weight pack, said lower center-rear strap is routed to a single strap connector having sufficient thickness, width, and length having a receiver hole, said lower center-rear strap is received at the lower area of said receiver hole of said single strap connector, said lower center-rear strap making a 90 degree turn is routed back to the upper edge at center of said stationary weight pack to be attached by said attachment means thereby having both ends of said lower center-rear strap attached to said stationary weight pack at the same area and at the same time.

4. An adjustable compact posture pack for posterior-thoracic counter balance according to claim 1 wherein said stationary weight pack has an upper center-rear strap having sufficient thickness width and length, having one end received at the upper area of said receiver hole of said single strap connector said upper center-rear strap making a 90 degree turn and having sufficient length is attached to itself by an attachment means, the other end of said upper center-rear strap is routed to an adjustment device having sufficient thickness, width, and length having a lower receiver hole and an upper receiver hole, said upper center-rear strap is received by both holes in such a manner to allow said upper center-rear strap to be adjusted to variable lengths, said upper center-rear strap is routed to said 3-way connector having a lower receiver hole, said upper center-rear strap is received by said lower receiver hole, then making a 90 degree turn is routed back to said adjustment device, said upper center-rear strap is received by said upper receiver hole then making a 90 degree turn having sufficient length is attached to itself by an attachment means.

5. An adjustable compact posture pack for posterior-thoracic counter balance according to claim 1 wherein said stationary weight pack having at least one upper stationary pocket having sufficient thickness, width, and length being attached by an attachment means to at least one lower stationary pocket having sufficient thickness, width, and length, said upper stationary pocket containing at least one weight material having sufficient thickness, width and length, and said lower stationary pocket containing at least one weight material having sufficient thickness, width and length, said upper stationary pocket and said lower stationary pocket having a first member attachment device located where said upper stationary pocket and said lower stationary pocket make contact, said first member attachment device upper half is attached to said upper stationary pocket by an attachment means and said first member attachment device lower half is attached to said lower stationary pocket by an attachment means.

6. An adjustable compact posture pack for posterior-thoracic counter balance according to claim 1 wherein said stationary weight pack having a removable weight pack having sufficient thickness, width and length having at least one removable pocket having sufficient thickness, width, and length, containing at least one weight material having sufficient thickness, width and length, said removable weight pack having a second member attachment device located at the horizontal center on the front side of said removable weight pack, said second member attachment device is attached by an attachment means to said removable weight pack, when said first member attachment device and said second member attachment device are pressed together each attaches itself to the other, when removing the said removable weight pack from said stationary weight pack the user applies a pulling pressure on the said removable weight pack causing said first member attachment device and said second member attachment device to detach.

* * * * *